(12) United States Patent
Lorant

(10) Patent No.: US 6,342,469 B1
(45) Date of Patent: Jan. 29, 2002

(54) MAKE-UP REMOVING AND/OR CLEANSING COSMETIC COMPOSITION IN THE FORM OF A WATER-IN-OIL EMULSION

(75) Inventor: Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/489,841

(22) Filed: Jan. 24, 2000

(30) Foreign Application Priority Data

Feb. 8, 1999 (FR) .............................. 99 01445

(51) Int. Cl.⁷ ................................. A61K 7/02
(52) U.S. Cl. .................... 510/136; 510/130; 510/417; 510/466
(58) Field of Search ................. 424/401, 402, 424/59; 510/118, 120, 121, 122, 136, 466

(56) References Cited

U.S. PATENT DOCUMENTS 5,972,315 A  *  10/1999  Voss et al. ................. 424/59
6,039,935 A  *  3/2000  Mohammadi ................. 424/59

OTHER PUBLICATIONS

Cosmetics and Toiletries, Wilfiried Umbach, p. 49, Ellis Horwood, 1991, West Sussex, England.*

* cited by examiner

Primary Examiner—Yogendra N. Gupta
Assistant Examiner—Gregory E. Webb
(74) Attorney, Agent, or Firm—Oblon, Spivak, McClelland, Maier & Neustadt, P.C.

(57) ABSTRACT

The invention relates to a make-up removing and/or cleansing cosmetic composition in the form of a water-in-oil emulsion and comprising (1) at least one silicone emulsifier, (2) at least one branched-chain hydrocarbonaceous oil and (3) at least one make-up removing oil chosen from esters of a fatty acid comprising at least 12 carbon atoms. The composition is fluid and may be used, for example, to remove make-up from the skin without any nuisance or irritation and with excellent effectiveness.

16 Claims, No Drawings

MAKE-UP REMOVING AND/OR CLEANSING COSMETIC COMPOSITION IN THE FORM OF A WATER-IN-OIL EMULSION

BACKGROUND OF THE INVENTION

1. Field of the Invention

The present invention relates to a make-up removing and/or cleansing cosmetic composition in the form of a water-in-oil emulsion comprising at least one silicone emulsifier, at least one branched-chain hydrocarbonaceous oil and at least one make-up removing oil, and to its use in removing make-up from and/or cleansing the skin, mucous membranes and/or eyes.

2. Description of the Background

The make-up removers and cleansers for the face conventionally used to date are compositions having a high concentration of fatty materials, the role of which, once applied to the skin, is to dissolve the various fatty substances present on the skin and in particular those which are present in make-up products, so as to remove them.

However, the use of such make-up removing compositions with a high content of fatty substances causes, at the time of their application, annoyance or discomfort which is reflected by a feeling of heaviness on the face or of a film on the eyes. The application of these compositions on the eyes can, furthermore, result in swelling of the eyelids.

The high concentration of fatty substances also presents problems of an unpleasant smell. It is consequently necessary to mask this smell by intense scenting, which causes other tolerance problems.

In addition, because of their "heavy" texture, these make-up removers lack freshness and are difficult to work. Furthermore, it is not easy to rinse them off. In fact, after they have been applied to the skin, such as that of the eyelids, rinsing using a tonic or water proves to be essential.

The need consequently remains for a cleansing and/or make-up removing composition which does not require rinsing after use on the skin, which exhibits a low concentration of fatty substances, thus avoiding the effect of "heaviness" on the skin, and which cleanses and/or removes make-up from the skin without the need to pass a cotton pad impregnated with the composition over the skin a number of times.

SUMMARY OF THE INVENTION

The inventors have now discovered, surprisingly, that a composition in the form of a water-in-oil emulsion, that is to say comprising an aqueous phase dispersed in an oily phase, comprising a silicone emulsifier, a branched-chain hydrocarbonaceous oil and a make-up removing oil makes it possible to obtain a composition which is fresh and light on application while being effective, in particular in cleansing and/or removing make-up from the skin, eyes or mucous membranes, without any nuisance or irritation and with excellent effectiveness.

Thus, the present invention provides a make-up removing and/or cleansing cosmetic composition in the form of a water-in-oil emulsion comprising an aqueous phase dispersed in an oily phase, and which also comprises:

at least one silicone emulsifier, at least one branched-chain hydrocarbonaceous oil and at least one make-up removing oil chosen from esters of a fatty acid comprising at least 12 carbon atoms.

The present invention also provides a method of removing make-up from and/or cleansing the skin, lips and/or eyes, comprising applying the composition to the skin, lips and/or eyes.

The present invention also provides a method of making the inventive composition.

The composition according to the present invention has the advantage of being light and fresh on application while carrying out removal of make-up or cleansing without rinsing being compulsory, which is particularly advantageous for skin suffering from certain skin conditions or in the cases of situations which are not very favourable to rinsing the skin, such as travelling. Furthermore, it leaves the skin soft, mat and non-sticky.

The composition according to the invention also makes possible its use in hot countries, where the use of make-up removers with an excessively high content of fatty substances gives a feeling of heaviness to the skin which is often unpleasant for the consumer A more complete appreciation of the invention and many of the attendant advantages thereof will be readily obtained as the same becomes better understood by reference to the following detailed description.

DETAILED DESCRIPTION OF THE INVENTION

Mention may be made, as silicone emulsifiers which can enter into the composition according to the invention, of dimethicone copolyols and alkyl dimethicone copolyols. Mention may be made, as dimethicone copolyol, of, for example, the mixture of dimethicone copolyol and of dimethicone (polydimethylsiloxane) (10/90) sold by Dow Corning under the name DC3225C. According to a preferred embodiment of the invention, use is made, as silicone emulsifier, of an alkyl dimethicone copolyol having an alkyl radical comprising from 10 to 22 carbon atoms, such as cetyl dimethicone copolyol, for example the product sold under the name Abil EM-90 by Goldschmidt; lauryl dimethicone copolyol, for example the mixture of approximately 91% lauryl dimethicone copolyol and of approximately 9% isostearyl alcohol sold under the name Q2-5200 by Dow Corning; and mixtures thereof.

The silicone emulsifier is preferably used in an amount of active material ranging, for example, from 0.2 to 10% and preferably from 1 to 6% by weight with respect to the total weight of the composition. These ranges include all specific values and subranges therebetween, such as 0.5, 1.5, 2, 3, 5 and 8% by weight.

The oily phase of the composition according to the invention comprises at least one branched-chain hydrocarbonaceous oil and at least one make-up removing oil chosen from esters of a fatty acid comprising at least 12 carbon atoms.

The branched-chain hydrocarbonaceous oil preferably comprises from 10 to 20 carbon atoms and can be chosen, for example, from the group consisting of isohexadecane, isododecane, isoparaffins and their mixtures.

The amount of hydrocarbonaceous oil(s) can range, for example, from 1 to 35% and preferably from 5 to 20% by weight with respect to the total weight of the composition. These ranges include all specific values and subranges therebetween, such as 2, 3, 8, 10, 15, 25 and 30% by weight.

The make-up removing oil is chosen from esters of a fatty acid comprising at least 12 carbon atoms. These esters are preferably obtained from a straight- or branched-chain alcohol comprising from 1 to 17 carbon atoms and from a straight- or branched-chain fatty acid comprising at least 12 carbon atoms and preferably from 14 to 22 carbon atoms. They are preferably mono- or diesters.

The make-up removing oil is preferably chosen from the group of the esters which do not comprise any unsaturation and/or any ether or hydroxyl group. More advantageously still, the make-up removing oil is a saturated ester which does not comprise any ether or hydroxyl group.

Thus, the make-up removing oil of the composition in accordance with the invention can be chosen in particular from the group consisting of 2-ethylhexyl palmitate (or octyl palmitate), 2-ethylhexyl myristate (or octyl myristate), isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate and their mixtures.

The amount of make-up removing oil(s) can range, for example, from 1 to 20% and preferably from 3 to 15% by weight with respect to the total weight of the composition. These ranges include all specific values and subranges therebetween, such as 2, 5, 8, 10, 12 and 18% by weight.

In addition, according to a preferred embodiment of the invention, the oily phase comprises at least one volatile silicone oil which can be chosen, for example, from cyclodimethylsiloxanes, such as cyclohexadimethylsiloxane (or cyclohexamethicone) and cyclopentadimethylsiloxane (or cyclopentamethicone), and their mixtures.

The amount of volatile silicone oil(s) can range, for example, from 1 to 30% and preferably from 5 to 20% by weight with respect to the total weight of the composition. These ranges include all specific values and subranges therebetween, such as 2, 3, 8, 10, 12, 15 and 25% by weight.

The oily phase can, in addition, comprise all the fatty substances and in particular the non-make-up removing oils, other than those indicated above, conventionally used in the cosmetics or dermatological fields. Mention may be made, as other oils capable of being present in the oily phase, of, for example, oils of vegetable origin, such as apricot kernel oil, synthetic oils, such as hydrogenated polyisobutene, non-volatile silicone oils and fluorinated oils. The other fatty substances capable of being present in the oily phase can be, for example, fatty acids, fatty alcohols and waxes, such as beeswax.

The oily phase of the emulsion can represent from 10 to 40% by weight and better still from 18 to 30% by weight of the total weight of the composition. These ranges include all specific values and subranges therebetween, such as 15, 20, 25, 30 and 35% by weight.

According to a specific embodiment of the invention, the composition additionally comprises one or more polyol alkyl esters. Mention may in particular be made, as polyol alkyl ester which can be used in the composition of the invention, of glycerol and/or sorbitan esters, for example polyglycerol isostearate, such as the product sold under the name Isolan GI 34 by Goldschmidt, sorbitan isostearate, such as the product sold under the name Arlacel 987 by ICI, glycerol sorbitan isostearate, such as the product sold under the name Arlacel 986 by ICI, and their mixtures.

When the composition comprises one or more polyol alkyl esters, the amount of polyol alkyl ester(s) can range, for example, from 0.05 to 5% and better still from 0.5 to 2% by weight with respect to the total weight of the composition. These ranges include all specific values and subranges therebetween, such as 0.1, 0.25, 1, and 3% by weight.

The composition of the invention can optionally comprise one or more fillers. The filler or fillers can be chosen, for example, from the group formed by polyamide particles and in particular those sold under the name Orgasol by Atochem; polyethylene powders; microspheres based on acrylic copolymers, such as those made of ethylene glycol dimethacrylate/lauryl methacrylate copolymer which are sold by Dow Coming under the name Polytrap; expanded powders, such as hollow microspheres and in particular the microspheres sold under the trade name Expancel by Kemanord Plast or under the trade name Micropearl F 80 ED by Matsumoto; powders formed of natural organic materials, such as maize, wheat or rice starches, which may or may not be crosslinked, such as the powders formed of starch which is crosslinked by octenylsuccinic anhydride which are sold under the name Dry-Flo by National Starch; silicone resin microbeads, such as those sold under the name Tospearl by Toshiba Silicone; and their mixtures.

The filler is preferably chosen from the microspheres sold under the trade name Expancel, which microspheres are particles of expanded terpolymer of vinylidene chloride, of acrylonitrile and of methacrylate, and in particular those sold under the references 551 DE 50 (particle size of approximately 40 $\mu$m), 551 DE 20 (particle size of approximately 30 $\mu$m and density of approximately 65 kg/m$^3$), 551 DE 12 (particle size of approximately 12 $\mu$m), 551 DE 80 (particle size of approximately 80 $\mu$m) and 461 DE 50 (particle size of approximately 50 $\mu$m). Use may also be made of microspheres formed of the same expanded terpolymer having a particle size of approximately 18 $\mu$m and a density of approximately 70 kg/m$^3$, known below as EL 23. Use may also be made of a mixture of these various particles.

The terpolymer particles indicated above can be dry or hydrated and can be obtained, for example, according to the processes of Patents and Patent Applications EP-A-056,219, EP-A-348,372, EP-A-486,080, EP-A-320,473, EP-A-1 12,807 and US-A-3,615,972. Each of these documents is incorporated herein by reference.

When the composition comprises fillers, the amount of filler(s) in the composition according to the invention can preferably range from 0.01% to 15% and better still from 0.1 to 5% by weight with respect to the total weight of the composition. These ranges include all specific values and subranges therebetween, such as 0.05, 0.2, 0.5, 1, 2, 8, 10 and 12% by weight.

The composition according to the invention can additionally comprise one or more salts and in particular a magnesium salt, such as magnesium sulfate. The amount of salt(s) can range, for example, from 0.1 to 5% and preferably from 0.5 to 1% by weight with respect to the total weight of the composition. These ranges include all specific values and subranges therebetween, such as 0.2, 0.75, 1.5, 2 and 3% by weight.

In addition, in a known way, the compositions of the invention can comprise adjuvants usual in the cosmetics or dermatological field, such as hydrophilic or lipophilic active principles, preservatives, antioxidants, fragrances, solvents, fillers, screening agents, coloring materials (pigments or dyes), basic agents (triethanolamine), acidic agents and lipid vesicles. These adjuvants are used in the proportions usual in the cosmetics or dermatological field, for example from 0.01 to 30% of the total weight of the composition, and they are, depending on their nature, introduced into the aqueous phase or into the oily phase of the emulsion or into vesicles. These adjuvants and their concentrations must be such that they do not modify the property desired for the composition.

According to a specific embodiment of the invention, the composition is preferably fluid, that is to say that it has a viscosity ranging from approximately 0.2 to 3 Pa·s (2 to 30 poises) and preferably from 0.6 to 2 Pa·s (6 to 20 poises), this viscosity being measured at approximately 25° C. using a "Rheomat Metler" viscometer equipped with a 2 rotor (for viscosities of less than 7 poises) or with a 3 rotor (for viscosities of greater than 7 poises).

However, if it is desired to obtain a less fluid composition, one or more lipophilic gelling agents, such as modified clays, for example bentones, fatty acid metal salts, for example aluminium stearate, hydrophobic silica or esters of glycol stearate, such as the acetyl ester of glycol stearate, sold under the name of Unitwix by Guardian, can be added thereto. These gelling agents can be used at concentrations ranging from 0.1 to 10%, preferably from 0.1 to 5% and better still from 0.1 to 3% of the total weight of the composition.

The make-up removing and/or cleansing composition according to the invention preferably comprises a physiological acceptable medium, i.e., a medium compatible with the skin, including the scalp, the mucous membranes (lips) and/or the eyes.

The composition according to the invention also has the advantage of having an excellent make-up removing effectiveness because of the continuous oily phase while being light, fresh and easy to spread and of making possible good make-up removal from and/or cleansing of the skin without attacking it, this composition being particularly well suited to cleansing dry and sensitive skin.

The invention consequently also relates to the cosmetic use of the composition as defined above in removing make-up from and/or cleansing the skin, lips and/or eyes.

The invention also relates to a cosmetic process for removing make-up from and/or cleansing the skin, lips and/or eyes, characterized in that a composition as described above is applied to the skin, lips and/or eyes.

This process may also comprise an optional rinsing step.

EXAMPLES

Having generally described this invention, a further understanding can be obtained by reference to certain specific examples which are provided herein for purposes of illustration only and are not intended to be limiting unless otherwise specified. The proportions by weight are given as percentage by weight with respect to the total weight of the composition.

Example 1

| Make-up removing milk for all skin types | |
|---|---|
| Oily phase: | |
| Cetyl dimethicone copolyol (Abil EM 90) | 2% |
| Isohexadecane | 5% |
| Cyclohexamethicone | 10% |
| Octyl palmitate | 10% |
| Filler: | |
| Expancel 551 | 0.5% |
| Aqueous phase: | |
| Glycerol | 5% |
| Magnesium sulfate | 0.5% |
| Preservatives | 0.4% |
| Water | q.s. for 100% |

Procedure: The filler is dispersed in the oily phase using a spatula and then the aqueous phase is dispersed very slowly, with vigorous stirring, in the mixture obtained.

A milk is thus obtained which is particularly pleasant to use and which exhibits very good make-up removing properties. Very smooth on application, it gently removes the make-up and the impurities without attacking or irritating the skin, which remains soft, mat and fresh.

Example 2

| Make-up removing milk for dry skin | |
|---|---|
| Oily phase: | |
| Cetyl dimethicone copolyol (Abil EM 90) | 1.5% |
| Isohexadecane | 5% |
| Cyclopentamethicone | 8% |
| Dioctyl adipate | 7% |
| Hydrogenated polyisobutene | 7% |
| Aqueous phase: | |
| Glycerol | 5% |
| Magnesium sulfate | 0.5% |
| Preservatives | 0.4% |
| Water | q.s. for 100% |

Procedure: The aqueous and oily phases are prepared separately and then the aqueous phase is dispersed very slowly, with vigorous stirring, in the oily phase.

A smooth and soft milk is thus obtained which exhibits very good sensory and make-up removing properties.

Example 3

| Make-up removing emulsion for dry and sensitive skin | |
|---|---|
| Oily phase: | |
| Cetyl dimethieone copolyol (Abil EM 90) | 1.5% |
| Isolan GI 34 | 0.5% |
| Isohexadecane | 5% |
| Cyclohexamethicone | 5% |
| Isopropyl palmitate | 5% |
| Apricot oil | 5% |
| Beeswax | 1% |
| Aqueous phase: | |
| Glycerol | 5% |
| Magnesium sulfate | 0.5% |
| Preservatives | 0.4% |
| Water | q.s. for 100% |

Procedure: The aqueous and oily phases are prepared separately under warm conditions and then the aqueous phase is dispersed very slowly, with vigorous stirring, in the oily phase.

A soft cream is obtained which melts on the skin. Soft on application, it spreads readily and makes possible the removal of the make-up and impurities gently and without rubbing, by simple wiping with a cotton pad. The skin remains clean and velvety and is soothed.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-01445, filed on Feb. 8, 1999, and incorporated herein by reference in its entirety.

What is claimed is:

1. A make-up removing and/or cleansing cosmetic composition, comprising:
   (i) an aqueous phase dispersed in an oily phase;
   (ii) at least one silicone emulsifier;
   (iii) at least one branched-chain hydrocarbonaceous oil; and
   (iv) from 3 to 20% by weight of at least one make-up removing oil selected from the group consisting of 2-ethylhexyl palmitate, 2-ethylhexyl myristate, isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexanoate, 2-ethylhexyl 2-ethylhexanoate, 2-ethylhexyl octanoate, 2-ethylhexyl-2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate, and mixtures thereof, based on the total weight of the composition, the composition existing as a water-in-oil emulsion.

2. The composition of claim 1, wherein the silicone emulsifier is an alkyl dimethicone copolyol having an alkyl radical comprising from 10 to 22 carbon atoms.

3. The composition of claim 1, wherein the silicone emulsifier is selected from the group consisting of cetyl dimethicone copolyol, lauryl dimethicone copolyol, and mixtures thereof.

4. The composition of claim 1, wherein the silicone emulsifier represents from 0.2 to 10% by weight as active material with respect to the total weight of the composition.

5. The composition of claim 1, wherein the branched-chain hydrocarbonaceous oil is selected from the group consisting of isohexadecane, isododecane, isoparaffins, and mixtures thereof.

6. The composition of claim 1, wherein the amount of hydrocarbonaceous oil(s) ranges from 1 to 35% by weight with respect to the total weight of the composition.

7. The composition of claim 1, further comprising at least one volatile silicone oil.

8. The composition of claim 7, wherein the amount of volatile silicone oil(s) ranges from 1 to 30% by weight with respect to the total weight of the composition.

9. The composition of claim 1, wherein the oily phase represents from 10 to 40% by weight of the total weight of the composition.

10. The composition of claim 1, further comprising a polyol alkyl ester.

11. The composition of claim 1, wherein the amount of polyol alkyl ester(s) ranges from 0.05 to 5% by weight with respect to the total weight of the composition.

12. The composition of claim 1, further comprising at least one filler.

13. The composition of claim 12, wherein the amount of filler(s) comprises from 0.01% to 15% by weight with respect to the total weight of the composition.

14. A method of making the composition of claim 1, comprising combining the aqueous phase, oily phase, and silicone emulsifier.

15. The composition of claim 1, wherein the amount of make-up removing oil(s) ranges from 3 to 15% by weight with respect to the total weight of the composition.

16. A method of removing make-up from and/or cleansing the skin, lips and/or eyes, comprising:
    applying a make-up removing and/or cleansing cosmetic composition in the form of a water-in-oil emulsion comprising:
    (i) an aqueous phase dispersed in an oily phase;
    (ii) at least one silicone emulsifier;
    (iii) at least one branched-chain hydrocarbonaceous oil; and
    (iv) at least one make-up removing oil selected from the group consisting of 2-ethylhexyl palmitate, 2-ethylhexyl myristate, isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexanoate, 2-ethylhexyl 2-ethylhexanoate, 2-ethylhexyl octanoate, 2-ethylhexyl-2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate, and mixtures thereof.

* * * * *